United States Patent
Kroll et al.

(10) Patent No.: US 7,203,546 B1
(45) Date of Patent: *Apr. 10, 2007

(54) SYSTEM AND METHOD OF IMPLEMENTING A PROPHYLACTIC PACER/DEFIBRILLATOR

(75) Inventors: Mark W. Kroll, Simi Valley, CA (US); Gabriel A. Mouchawar, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 379 days.

This patent is subject to a terminal disclaimer.

(21) Appl. No.: 10/761,907

(22) Filed: Jan. 20, 2004

(51) Int. Cl.
    *A61N 1/368* (2006.01)
(52) U.S. Cl. .................. 607/34; 607/4; 607/5
(58) Field of Classification Search ............ 607/2, 607/4–8, 9, 34, 15, 121–122
    See application file for complete search history.

(56) References Cited

U.S. PATENT DOCUMENTS

| | | | |
|---|---|---|---|
| 4,787,389 A * | 11/1988 | Tarjan | 607/4 |
| 4,796,630 A * | 1/1989 | Regna | 607/9 |
| 4,942,501 A * | 7/1990 | MacFarlane et al. | 361/523 |
| 5,372,605 A | 12/1994 | Adams et al. | 607/5 |
| 5,376,103 A * | 12/1994 | Anderson et al. | 607/5 |
| 5,439,482 A | 8/1995 | Adams et al. | 607/5 |
| 5,545,183 A * | 8/1996 | Altman | 607/5 |
| 5,554,174 A * | 9/1996 | Causey, III | 607/5 |
| 5,558,962 A | 9/1996 | Marincic et al. | 429/233 |
| 5,591,212 A * | 1/1997 | Keimel | 607/5 |
| 5,755,742 A * | 5/1998 | Schuelke et al. | 607/27 |
| 5,836,973 A | 11/1998 | Kroll | 607/5 |
| 5,919,211 A | 7/1999 | Adams | 607/5 |
| 6,044,295 A * | 3/2000 | Pilz et al. | 607/4 |
| 6,283,985 B1 | 9/2001 | Harguth et al. | 607/1 |
| 6,562,255 B1 * | 5/2003 | Feger | 252/62.2 |
| 2002/0035380 A1 | 3/2002 | Rissmann et al. | 607/4 |
| 2004/0243183 A1 * | 12/2004 | Norton et al. | 607/5 |

FOREIGN PATENT DOCUMENTS

| | | |
|---|---|---|
| EP | 0650383 B1 | 7/1993 |
| EP | 0746048 A2 | 5/1996 |
| EP | 0746048 A3 | 5/1996 |
| WO | WO 95/09030 A2 | 4/1995 |
| WO | WO 95/09030 A3 | 4/1995 |
| WO | WO 96/22811 | 8/1996 |

* cited by examiner

*Primary Examiner*—Robert E. Pezzuto
*Assistant Examiner*—Jessica L. Reidel

(57) ABSTRACT

The prophylactic pacer/defibrillator is configured to deliver shocking therapy in response to a single episode of ventricular fibrillation, as well as delivering otherwise conventional pacing therapy. By providing "one shot" defibrillation capabilities a patient who is not at significant risk of ventricular fibrillation—and hence is not a candidate for a full-service implantable cardioverter defibrillator (ICD)—can receive defibrillation therapy in the event ventricular fibrillation should nevertheless occur. Once the prophylactic pacer/defibrillator has delivered shocks to terminate the single episode of ventricular fibrillation, the patient returns to his or her physician to have the device removed and a full-service ICD implanted, so that any additional episodes of ventricular fibrillation may be addressed by the full-service ICD.

14 Claims, 11 Drawing Sheets

SYSTEM AND METHOD OF IMPLEMENTING A PROPHYLACTIC PACER/DEFIBRILLATOR

FIELD OF THE INVENTION

The invention relates to implantable medical devices and more particularly to implantable pacemakers and implantable cardioverter defibrillators (ICDs).

BACKGROUND

A pacemaker is a medical device for implant within a patient, which recognizes various arrhythmias such as an abnormally slow heart rate (bradycardia) or an abnormally fast heart rate (tachycardia) and delivers electrical pacing pulses to the heart in an effort to remedy the arrhythmia. An ICD is a device, also for implant within a patient, which additionally or alternatively recognizes atrial fibrillation (AF) or ventricular fibrillation (VF) and delivers electrical shocks to terminate the fibrillation. Herein, the term "cardioversion" refers to the delivery of shocking pulses intended to defibrillate the atria. "Defibrillation" refers to the delivery of shocking pulses intended to defibrillate the ventricles.

An exemplary ICD 10 along with various sensing/pacing/shocking leads are shown in FIG. 1. To sense atrial cardiac signals and to provide right atrial chamber pacing therapy, the ICD is coupled to an implantable right atrial lead 20 having an atrial tip electrode 22 and an atrial ring electrode 23. To sense left atrial and ventricular cardiac signals and to provide left chamber pacing therapy, the ICD is coupled to a "coronary sinus" lead 24 designed to receive atrial and ventricular cardiac signals and to deliver: left ventricular pacing therapy via a left ventricular tip electrode 26; left atrial pacing therapy via a left atrial ring electrode 27; and cardioversion shocks via a left atrial coil electrode 28. A right ventricular lead 30 includes a right ventricular tip electrode 32, a right ventricular ring electrode 34, a right ventricular (RV) coil electrode 36 and a superior vena cava (SVC) coil electrode 38. The right ventricular lead is capable of receiving cardiac signals and delivering pacing stimulation via the tip and ring electrodes 32 and 34 and delivering defibrillation shocks via coil 36 and SVC coil electrode 38. Cardioversion shocks are typically delivered with up to 10 joules of energy. Defibrillation shocks are much stronger and typically employ up to 40 or more joules of energy. Both cardioversion shocks and defibrillation shocks are delivered at high voltages, on the order of 800 volts. ICDs are typically designed to be capable of delivering at least a hundred defibrillation shocks.

To withstand the high voltages and large quantities of energy required for cardioversion and defibrillation shocks and to permit delivery of a large number of shocks over the lifetime of the device, ICDs and their leads are designed as robustly as possible. To this end, ICDs typically include one or more silver vanadium oxide (SVO) batteries along with one or more large capacitors, each formed of aluminum oxide ($Al_2O_3$). The SVO batteries provide power for all cardioversion and defibrillation shocks as well as for all pacing and monitoring functions. Once the ICD is implanted, it is not intended to be removed, hence the SVO power source used therein must be sufficiently large to provide power to deliver a hundred or more of defibrillation shocks, as well as to provide power for long-term pacing and sensing functions, typically for the lifetime of the patient. In the rare case where the power cell becomes depleted, the ICD is replaced with another similar ICD.

The SVO batteries and the aluminum oxide capacitors are quite large in size and weight and, to ensure that the capacitors can be promptly be charged to high-voltages upon detection of defibrillation, the capacitors are periodically reformed, i.e. the capacitors are charged to capacity every three months or so, even if no shock is required. By periodically reforming the aluminum oxide capacitor, ten seconds or more can be reduced in charge time as compared to a capacitor that has not been reformed, thus allowing an initial defibrillation pulse to be delivered as quickly as possibly upon detection of an episode of ventricular fibrillation. Charge delivered to the capacitor during reformation is dumped from the capacitor through a dump resistor provided within the implanted device so that the energy may be dissipated as heat.

As noted, the SVC coil, the right ventricular coil, and the right ventricular tip and ring electrodes are all provided within a single right ventricular lead (lead 30 of FIG. 1). Because the lead must accommodate the currents and voltages required for numerous cardioversion and defibrillation shocks, the lead typically employs electrical insulation along its entire length. The insulation is provided, in part, to ensure that defibrillation shocks delivered to the right ventricular coil are not short-circuited.

Additionally, cut-off switches are provided within the ICD to help prevent shocking currents from being conducted back through the leads and into the device electronics, which might damage or disable the device electronics. In particular, cut-off switches are provided on all pacing outputs (tip and ring) leads. The switches also help prevent tissue necrosis from occurring within myocardial tissue near the electrodes as a result of "in rush" current. For example, if cut-off switches were not provided, current delivered by the right ventricular coil electrode would likely pass through myocardial tissue and into the right ventricular tip electrode. Current densities near the tip electrode can damage myocardial tissue, particularly with delivery of numerous shocks. In this regard, within most ICDs, the right ventricular tip and ring electrodes are held at voltages intermediate the voltage of the device case and the voltage of the right ventricular coil. Typically, a voltage difference between the case and the right ventricular coil upon delivery of a defibrillation pulse is 800 volts. Hence, there is usually about a 400 volt difference between the device case and the right ventricular tip and ring electrodes and another 400 volt difference between the right ventricular tip and ring electrodes and the right ventricular coil electrode. Similar voltage differences may occur between the atrial tip and ring electrodes and the device case and the right ventricular coil. These large voltage differences necessitate the cut-off switches. However, such switches are bulky and consume considerable space within the ICD housing. In addition to the switches themselves, additional circuitry and microprocessor logic must be provided to coordinate the use of the switches and, should one of the switches fail, the device electronics are in jeopardy.

The aforementioned features are illustrated in the diagram of FIG. 2. Briefly, a single SVO power source 51 provides all power for the device including power to operate control circuitry 52, which controls all pacing, monitoring, capacitor reformation, cardioversion and defibrillation control functions. The single power supply also provides power for delivering pacing pulses through right atrial, left atrial and right ventricular tip and ring electrodes as well as to provide biphasic cardioversion and the defibrillation shocks via the left and right ventricular coil electrodes, the left atrial coil, and the SVC electrode. Exemplary electrode voltages are listed in FIG. 2. These are merely provided to illustrate voltage differences—actual absolute voltages may differ.

During pacing, switches 53, provided along the pacing/sensing leads, are closed to allow pacing and sensing. For cardioversion or defibrillation, a capacitor charging switch 54 is toggled at high frequencies to begin charging an aluminum oxide capacitor 55 via a voltage transformer 56. For cardioversion, up to ten joules are stored within the capacitor. Just prior to delivery of the cardioversion shock, switches 53 are opened to prevent current from propagating into control circuitry to via the pacing and sensing leads. Then appropriate switches within shock switching circuitry 57 are closed to route the energy stored with capacitor into the atria as a biphasic shocking pulse using, for example, the AL coil and the case as electrodes. For defibrillation, about 40 joules of energy are stored within the capacitor and then appropriate switches within switching circuitry 57 are closed to route the energy into the ventricles as a biphasic pulse using the right ventricular coil electrode in combination with either the left ventricular coil, the SVC or the case. In early devices, defibrillation shocks were usually delivered between the RV coil and the SVC coil. More recent devices typically deliver the defibrillation shock between the ventricular coil electrodes and the device can. The RV-SVC coil delivery is still employed in some patients, as it is believed that a lower defibrillation threshold can be achieved, i.e. less energy may be required within the shock to defibrillate the heart. In nay case, once a cardioversion or defibrillation shock is delivered, switches 53 are again closed to allow sensing to determine whether the shock was successful and, if not, switches 53 are again opened and additional cardioversion or defibrillation shocks are delivered to the heart of the patient.

If no shocks are delivered for about three months, control circuitry 52 initiates a capacitor reformation process wherein capacitor 55 is charged to capacity, without delivering a shock to the patient. After reformation, a dump resistor switch 58 maybe closed to allow the charge of the capacitor to be dissipated through a dump resistor 59. The dump resistor is also used if charge stored on the capacitor exceeds the programmed therapy value. The capacitor reformation process is summarized in FIG. 3. Briefly, a capacitor reformation timer is initially set at step 60, typically to time a three-month period. Then, beginning at step 61, the ICD monitors cardiac rhythm to deliver pacing therapy and to detect atrial or ventricular fibrillation and, if fibrillation is detected, the internal capacitor is charged and an appropriate shock is delivered, at step 62. Once a shock is delivered, the capacitor reformation timer is then reset at step 60 since the process of charging the capacitor to deliver the shock serves to reform the capacitor. The device then continues to monitor for atrial or ventricular fibrillation, at step 61. So long as no fibrillation is detected, the device simply continues delivering any needed pacing therapy and monitoring for fibrillation. Eventually, if no shocks are delivered, the timer expires and, at step 63, the ICD performs the capacitor reformation procedure wherein the capacitor is charged to its maximum capacity. Note, however, that dumping is not a requirement. Alternatively, the charge can be allowed to dissipate internally via leakage. In any case, the reformation timer is reset at step 60. As noted, by periodically reforming the capacitor if no shocks are delivered, the capacitor can be more quickly charged to capacity when a shock is required.

As can be appreciated, the need to provide the aforementioned ICD features and lead features for accommodating the large currents and voltages required for defibrillation results in an ICD and lead assembly that is large, heavy, complex and quite expensive. Hence, ICDs are typically implanted only within the patients who are at a significant risk of ventricular fibrillation, such as patients who have had a previous myocardial infarction. More specifically, ICDs are usually only implanted within patients classified as Class I patients within the ICD implantation guidelines of Table I.

Class I
 1. Cardiac arrest due to VF or VT not due to a transient or reversible cause. (Level of evidence: A)
 2. Spontaneous sustained VT. (Level of evidence: B)
 3. Syncope of undetermined origin with clinically relevant, hemodynamically significant sustained T or VF induced at electrophysiological study when drug therapy is ineffective, not tolerated, or not preferred. (Level of evidence: B)
 4. Nonsustained VT with coronary disease, prior MI, LV dysfunction, and inducible VF or sustained VT at electrophysiological study that is not suppressible by a Class I antiarrhythmic drug. (Level of evidence: B)

Class IIa
 None

Class IIb
 1. Cardiac arrest presumed to be due to VF when electrophysiological testing is precluded by other medical conditions. (Level of evidence: C)
 2. Severe symptoms attributable to sustained ventricular tachyarrhythmias while awaiting cardiac transplantation. (Level of evidence: C)
 3. Familial or inherited conditions with a high risk for life-threatening ventricular tachyarrhythmias such as long QT syndrome or hypertrophic cardiomyopathy. (Level of evidence: B)
 4. Nonsustained VT with coronary artery disease, prior MI, and LV dysfunction, and inducible sustained VT or VF at electrophysiological study. (Level of evidence: B)
 5. Recurrent syncope of undetermined etiology in the presence of ventricular dysfunction and inducible ventricular arrhythmias at electrophysiological study when other causes of syncope have been excluded. (Level of evidence: C)

Class III
 1. Syncope of undetermined cause in a patient without inducible ventricular tachyarrhythmias. (Level of evidence: C)
 2. Incessant VT or VF. (Level of evidence: C)
 3. VF or VT resulting from arrhythmias amenable to surgical or catheter ablation; for example, atrial arrhythmias associated with the Wolff-Parkinson-White syndrome, right ventricular outflow tract VT, idiopathic left ventricular tachycardia or fascicular Vt. (Level of evidence: C)
 4. Ventricular tachyarrhythmias due to a transient or reversible disorder (e.g., AMI, electrolyte imbalance, drugs, trauma). (Level of evidence: C)
 5. Significant psychiatric illnesses that may be aggravated by device implantation or may preclude systematic follow-up. (Level of evidence: C)
 6. Terminal illnesses with projected life expectancy $</=6$ months. (Level of evidence: C)
 7. Patients with coronary artery disease with LV dysfunction and prolonged QRS duration in the absence of spontaneous or inducible sustained or nonsustained VT who are undergoing coronary bypass surgery. (Level of evidence: B)

8. Class IV drug-refractory congestive heart failure in patients who are not candidates for cardiac transplantation. (Level of evidence: C)

Level of evidence: Level A=well-designed, controlled clinical trials; B=cohort studies; C=expert opinion Table I Moreover, to maximize the lifetime of the SVO power source, the ICD must be programmed to deliver shocks with the lowest magnitude sufficient to reliably defibrillate the ventricles (plus some safety margin). Accordingly, the physician usually must perform a ventricular fibrillation induction test wherein the physician triggers ventricular fibrillation within the patient then controls the ICD to deliver various shocks of differing magnitudes so as to determine the minimum shocking energy sufficient to reliable defibrillate the patient. The fibrillation induction procedure is summarized by FIG. 4. Briefly, prior to implant of an ICD, a determination is made as to whether the patient is at high risk of ventricular fibrillation, i.e. a determination is made as to whether the patient is classified within the Class 1. Assuming class 1, then an ICD, such as the one illustrated in FIGS. 1 and 2, is implanted within the patient, along with leads capable of providing for pacing, cardioversion and defibrillation. At step 72, the physician sets the shock magnitude for defibrillation shocks to a low test magnitude then, at step 73, induces ventricular fibrillation within the heart of the patient. At step 74, the implanted ICD detects the fibrillation and delivers a test shock at the selected shock magnitude. If the shock does not successfully defibrillate the heart, then the ICD increases the shock magnitude, at step 75, and another shock is delivered. Once a shock successfully defibrillates the heart, then, at step 76, a safety margin is added to the shock magnitude that proved successful and, at step 77, the patient is sent home with the ICD set to deliver pacing therapy, if needed, and to respond to potentially numerous episodes of atrial or ventricular fibrillation, should such episodes arise. In the example FIG. 4, the induction test is performed to set the shock magnitude by selectively increasing from a minimum shock magnitude. In other examples, the test begins with a maximum shock magnitude, which is incrementally decreased. Still other specific approaches can be employed. The intentional induction of ventricular fibrillation within a patient is, of course, a risky procedure and hence many physicians are reluctant to perform the procedure and many patients are reluctant to undergo the procedure. Within patients for whom induction testing is performed, the associated costs of the overall implantation of the ICD are significant increased. This is another reason why ICDs are typically only implanted within patients at significant risk of ventricular fibrillation.

Despite the significant costs, an ICD can be lifesaving and hence ICDs are now commonly implanted in patients who are at a high risk of ventricular fibrillation, i.e. Class 1 patients. However, ventricular fibrillation sometimes also arises within patients who do not appear to be at significant risk (i.e. non-Class 1 patients), including the patients who would otherwise receive only a conventional pacemaker. Within such patients, should ventricular fibrillation nevertheless occur, it often proves fatal because there is typically not sufficient time for paramedics to arrive with an external defibrillator to defibrillate the heart.

Accordingly, it would be highly desirable to provide an implantable medical device capable of delivering defibrillation therapy for implantation in patients not perceived to be at high risk of ventricular fibrillation (i.e. for use in non-Class 1 patients.) Such a device would not be as bulky, heavy, and expensive as a "full-service" ICD of the type described above and would not require fibrillation induction testing.

SUMMARY

In accordance with one illustrative embodiment, a prophylactic pacer/defibrillator is provided, which comprises an otherwise conventional pacemaker provided with minimal defibrillation enhancements to allow for delivering shocking therapy in response to a single episode of ventricular fibrillation. To this end, the implanted device and its leads are configured to accommodate the delivery of a relatively small number (e.g., less than ten, for example six) defibrillation shocks for purposes of terminating a single episode of ventricular fibrillation. By providing "one shot" defibrillation capabilities within an otherwise conventional pacemaker, a patient who is not at significant risk of ventricular fibrillation (and hence is not a candidate for a "full-service" ICD) can nevertheless receive defibrillation therapy in the event ventricular fibrillation should nevertheless occur. Once the prophylactic pacer/defibrillator has delivered shocks to terminate the single episode of ventricular fibrillation, the patient returns to his or her physician to have the prophylactic pacer/defibrillator removed and a full-service ICD implanted, so that any additional episodes of ventricular fibrillation may be responded to by the full-service ICD.

To provide prophylactic defibrillation capability within an otherwise conventional pacemaker, one or more of the following innovations is incorporated within the device itself or within the leads used therewith.

A shocking capacitor is provided which does not require reformation, such as a capacitor formed of tantalum. By providing a capacitor that does not require reformation, the power source of the device need not be capable of providing a sufficient charge to reform the capacitor on a periodic basis. Hence, a smaller, lighter and less expensive power supply can be provided. Additionally, the tantalum capacitor is itself also smaller than the aluminum oxide capacitors typically employed within full-service ICDs. In addition, reformation circuitry and logic that would otherwise be required to control the reformation process need not be included, thus achieving further savings in cost and complexity. As an alternative, an otherwise conventional aluminum oxide capacitor may be employed but not periodically reformed. Again, reformation logic and circuitry are not required. In addition, because reformation is not performed, no dump resistor is required for dumping charge from the capacitor. Hence, still further savings in size, weight, complexity and cost are achieved as compared to a full-service ICD that requires a large dump resistor capable of dissipating the energy stored within the capacitor during reformation.

In one embodiment, separate power sources are provided for pacing/sensing and for shocking. Preferably, a carbon monofluoride ($CF_x$) battery is provided for powering all pacing/sensing functions; whereas a lithium magnesium oxide ($LiMnO_2$) battery is provided for powering the few shocking pulses. By powering the pacing/sensing functions with one battery and the shocking functions with another battery, the shocking battery may be completely depleted during the delivery of defibrillation shocks without interfering with pacing/sensing functions, which can reliably continue until the device is replaced. Moreover, since the device is intended to be capable of delivering only enough shocks to respond to a single episode of ventricular fibrillation, the shocking battery need not be as large and expensive as shocking batteries typically employed within full-service ICDs, which instead must be capable of delivering potentially a hundred defibrillation shocks. Accordingly, considerable savings in terms of size, weight and cost are achieved. Additionally, because the shocking power source can accommodate only a minimal number of shocks, fibrillation induction testing is not performed using the device, though it can instead be performed in conjunction with an external defibrillator. Hence, further cost savings are achieved as compared to full-service ICDs that require induction testing to be performed by physician. In addition to cost savings, the risks associated with induction testing (such as the fact that ventricular fibrillation, once induced, may be difficult to terminate) are avoided.

No SVC coil is provided or, if one is provided, it is hardwired into the device case, i.e. no cut-off switch is provided on the SVC output. An SVC coil need not be provided, in part, because reduction of the defibrillation threshold is not critical since the device is intended to respond to only a single episode of fibrillation. Also, a less complex right ventricular lead may be employed since it need not include the SVC coil. Additionally, without the SVC coil, less electrical insulation is required along the lead itself since there is less risk of currents generated by the right ventricular coil short-circuiting into an SVC coil lead. Instead, thick insulation is only required near the device can to prevent shorting between the base of the lead and the device can. If an SVC coil is employed, it is preferably used only as a return electrode for defibrillation shocks delivered via the right ventricular lead and so a cut-off switch is not required.

Crowbar shunt diodes are provided along the various pacing/sensing leads rather than cut-off switches. In this regard, preferably, zener diodes are provided between the each pair of leads within the device case to ensure that any currents conducting inbound to the device electronics along one of the leads is routed outbound on another lead, thus sparing of the device electronics from potentially damaging electrical currents. Zener diodes are typically much smaller and less expensive than cut-off switches and no complicated circuitry is required to control the opening and closing of the switches. Accordingly, savings are again achieved in terms of size, weight, complexity and cost. Note that the zener diodes need not be sufficiently robust to accommodate numerous defibrillation shocks. They need only be sufficient to accommodate shocks delivered in response to a single episode of ventricular fibrillation. In addition, because only a few shocks are ever generated, tissue necrosis caused by in-rush currents at the tips of the shunted leads is not a problem.

The right ventricular tip and ring electrodes are set to voltages close to the voltage of the right ventricular coil. As such, during the delivery of a defibrillation shocks, there is only a small voltage difference between the shocking coil, the right ventricular tip and ring electrodes and hence any currents generated therein are likely to be minimal. This allows a reduction in the number of the shunt diodes that would otherwise be required. For example, by setting the ventricular ring electrodes to the same voltage as the right ventricular coil electrode, no diodes need to be provided along the right ventricular ring lead. This provides still further benefits in terms of size, weight, cost and complexity.

Alternatively, no ventricular ring electrode is employed at all. Rather the ventricular coil is used as the return electrode for pacing/sensing functions with the ventricles. This provides for still further reductions in the cost and complexity of both the implanted device as well as the lead assembly.

No left atrial coil is provided and no cardioversion capability is provided. Accordingly, circuitry and logic otherwise required within a full-service ICD to perform cardioversion need not be incorporated, with attendant savings in cost and complexity. Hence, various improvements are provided to help facilitate the implementation of the prophylactic pacer/defibrillator, capable of delivering pacing therapy and also capable of responding to a single episode of the ventricular fibrillation. Since the prophylactic pacer/defibrillator is considerably smaller, lighter, less complex, and less expensive than a full-service ICD, and because the ventricular fibrillation induction testing is not required, the prophylactic pacer/defibrillator can be easily and inexpensively implanted within patients that would otherwise merely receive a pacemaker (i.e. non-Class 1 VF patients). Hence, should such patients suffer an episode of ventricular fibrillation, the device can respond by delivering shocks to terminate the fibrillation, thereby likely saving the patient's life.

Other objects, features advantages will be apparent from the descriptions that follow.

BRIEF DESCRIPTION OF THE DRAWINGS

Further features and advantages may be more readily understood by reference to the following description taken in conjunction with the accompanying drawings, in which.

DESCRIPTION OF THE PREFERRED EMBODIMENTS

The following description is of the best mode presently contemplated. This description is not to be taken in a limiting sense but is made merely for the purpose of describing the general principles of the prophylactic ICD. The scope of the invention should be ascertained with reference to the issued claims. In the description that follows, like numerals or reference designators will be used to refer to like parts or elements throughout.

Overview of Prophylactic Pacer/Defibrillator System

Figure 5:
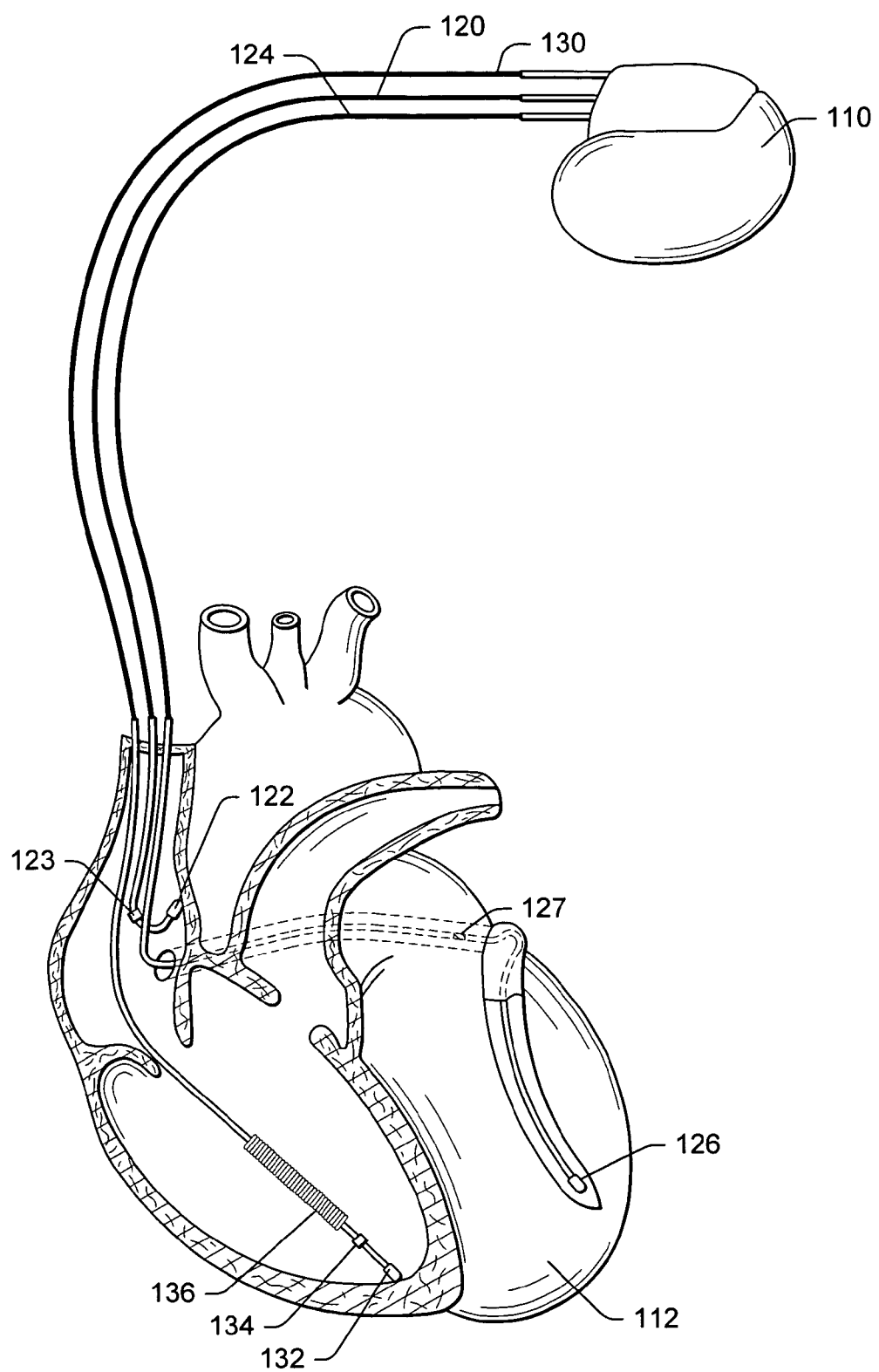
FIG. 5 illustrates a prophylactic pacer/defibrillator device and three leads for delivering ventricular defibrillation shock therapy in response to a single episode of ventricular fibrillation in accordance with an exemplary embodiment, as well as for delivering multi-chamber pacing therapy.

FIG. 5 illustrates a prophylactic defibrillation stimulation device 110 (also referred to herein as a prophylactic pacer/defibrillator) in electrical communication with a heart 112 by way of three leads, 120, 124 and 130, suitable for delivering multi-chamber pacing stimulation therapy and ventricular defibrillation shock therapy. To sense atrial cardiac signals and to provide right atrial chamber stimulation therapy, device 110 is coupled to an implantable right atrial lead 120 having at least an atrial tip electrode 122 and an atrial ring electrode 123, which typically is implanted in the right atrial appendage. To sense left atrial and ventricular cardiac signals and to provide left chamber pacing therapy, the stimulation device 110 is coupled to a "coronary sinus" lead 124 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 124 is designed to receive atrial and ventricular cardiac signals and to deliver left ventricular pacing therapy using at least a left ventricular tip electrode 126, left atrial pacing therapy using at least a left atrial ring electrode 127.

The stimulation device 110 is also shown in electrical communication with the heart by way of an implantable right ventricular lead 130 having, in this embodiment, a right ventricular tip electrode 132, a right ventricular ring electrode 134 and a right ventricular (RV) coil electrode 136. Typically, the right ventricular lead 130 is transvenously inserted into the heart so as to place the right ventricular tip electrode 132 in the right ventricular apex so that the RV coil electrode will be positioned in the right ventricle. Accordingly, the right ventricular lead 130 is capable of receiving cardiac signals, and delivering stimulation in the form of pacing and shock therapy to the right ventricle.

Since the lead system does not include an SVC coil and the prophylactic pacer/defibrillator is only intended to deliver a small number (e.g., less than ten, such as about six) shocks, the various leads need not employ as much electrical insulation as leads used with full-service ICDs (which is provided to prevent shorting between the device case and the various leads.) As shown in FIG. 5, enhanced insulation is instead only provided near the device case.

Figure 6:
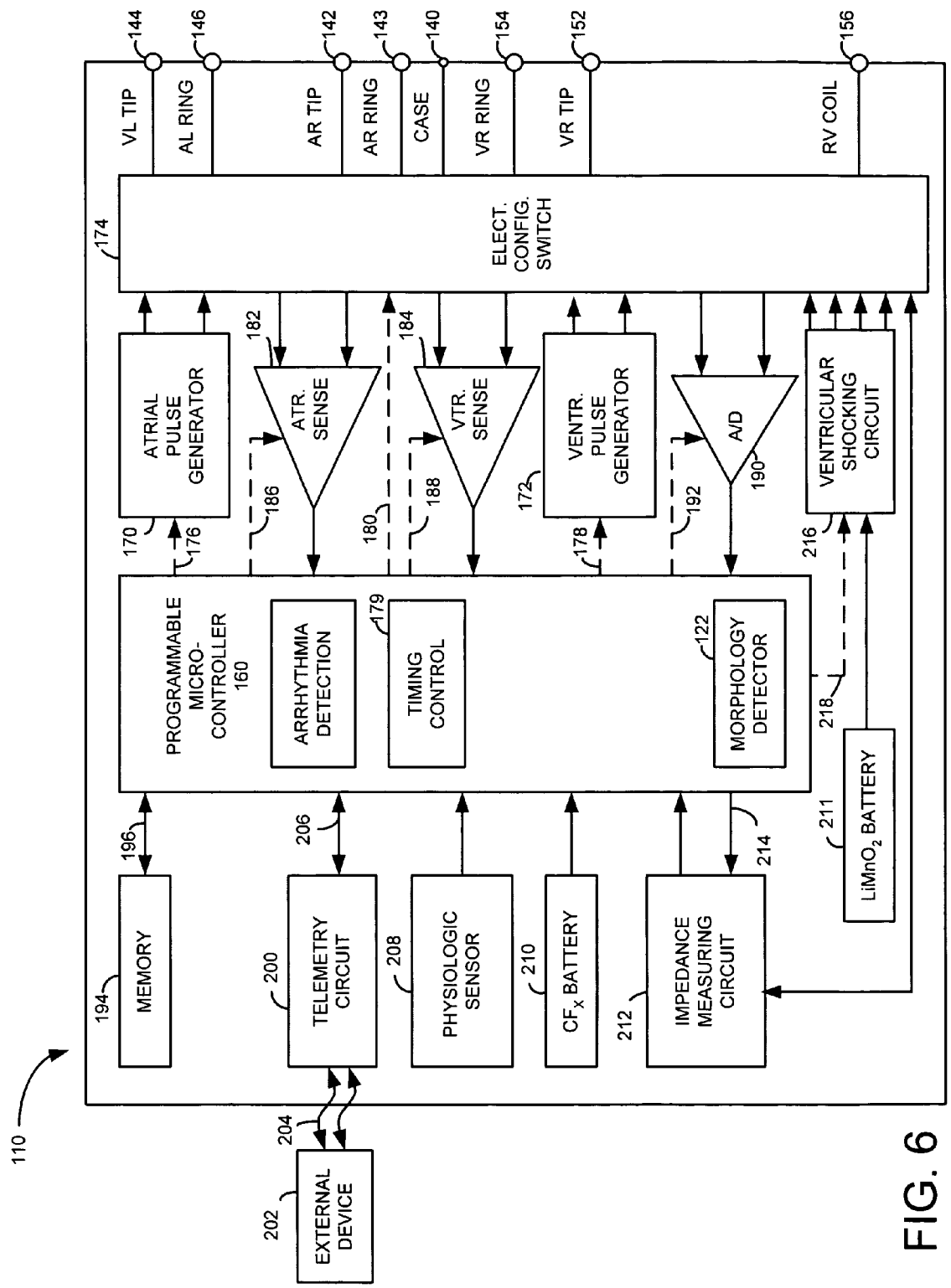
FIG. 6 is a functional block diagram of the prophylactic pacer/defibrillator device of FIG. 5 illustrating the basic elements of the device.

FIG. 6 provides a simplified block diagram of internal components of the prophylactic pacer/defibrillator of FIG. 5, which is capable of treating both fast and slow arrhythmias with stimulation therapy, including defibrillation and pacing stimulation. While a particular multi-chamber prophylactic pacer/defibrillator is shown, this is for illustration purposes only, and one of skill in the art could readily duplicate, eliminate or disable the appropriate circuitry in any desired combination to provide a device capable of treating the appropriate chamber(s) with cardioversion as well as defibrillation and pacing stimulation.

The housing 140 for the prophylactic pacer/defibrillator, shown schematically in FIG. 6, is often referred to as the "can", "case" or "case electrode" and may be programmably selected to act as the return electrode for all "unipolar" modes. The housing 140 may further be used as a return electrode alone or in combination with one or more of the coil electrode 136, for ventricular shocking purposes. The housing 140 further includes a connector (not shown) having a plurality of terminals, 142, 143, 144, 146, 152, 154 and 156 (shown schematically and, for convenience, the names of the electrodes to which they are connected are shown next to the terminals). As such, to achieve right atrial sensing and pacing, the connector includes at least a right atrial tip terminal ($A_R$ TIP) 142 adapted for connection to the atrial tip electrode 122 and at least a right atrial ring terminal ($A_R$ RING) 143 adapted for connection to the atrial ring electrode 123. To achieve left chamber sensing, pacing and left ventricular shocking, the connector includes at least a left ventricular tip terminal ($V_L$ TIP) 144, a left atrial ring terminal ($A_L$ RING) 146, which are adapted for connection to the left ventricular ring electrode 126, the left atrial tip electrode 127, respectively. To support right chamber sensing and pacing, the connector further includes a right ventricular tip terminal ($V_R$ TIP) 152, a right ventricular ring terminal ($V_R$ RING) 154, a right ventricular shocking terminal ($R_V$ COIL) 156, which are adapted for connection to the right ventricular tip electrode 132, right ventricular ring electrode 134, the RV coil electrode 136, respectively.

At the core of the prophylactic pacer/defibrillator is a programmable microcontroller 160, which controls the various modes of stimulation therapy. As is well known in the art, the microcontroller 160 typically includes a microprocessor, or equivalent control circuitry, designed specifically for controlling the delivery of stimulation therapy and may further include RAM or ROM memory, logic and timing circuitry, state machine circuitry, and I/O circuitry. Typically, microcontroller 160 includes the ability to process or monitor input signals (data) as controlled by a program code stored in a designated block of memory. The details of the design and operation of microcontroller 160 are not critical. Rather, any suitable microcontroller may be used that carries out the functions described herein. The use of microprocessor-based control circuits for performing timing and data analysis functions are well known in the art.

As shown in FIG. 6, an atrial pulse generator 170 and a ventricular pulse generator 172 generate pacing stimulation pulses for delivery by the right atrial lead 120, the right ventricular lead 130, and/or the coronary sinus lead 124 via an electrode configuration switch 174. It is understood that in order to provide stimulation therapy in each of the four chambers of the heart, the atrial and ventricular pulse generators, 170 and 172, may include dedicated, independent pulse generators, multiplexed pulse generators or shared pulse generators. The pulse generators, 170 and 172, are controlled by the microcontroller 160 via appropriate control signals, 176 and 178, respectively, to trigger or inhibit the stimulation pulses. The microcontroller 160 further includes timing control circuitry 179 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, post ventricular atrial refractory period (PVARP) intervals, noise detection windows, evoked response windows, alert intervals, marker channel timing, etc., which is well known in the art. Switch 174 includes a plurality of switches for connecting the desired electrodes to the appropriate I/O circuits, thereby providing complete electrode programmability. Accordingly, switch 174, in response to a control signal 180 from the microcontroller 160, determines the polarity of the stimulation pulses (e.g., unipolar, bipolar, combipolar, etc.) by selectively closing the appropriate combination of switches (not shown) as is known in the art.

Atrial sensing circuits 182 and ventricular sensing circuits 184 may also be selectively coupled to the right atrial lead 120, coronary sinus lead 124, and the right ventricular lead 130, through the switch 174 for detecting the presence of cardiac activity in each of the four chambers of the heart. Accordingly, the atrial (ATR. SENSE) and ventricular (VTR. SENSE) sensing circuits, 182 and 184, may include dedicated sense amplifiers, multiplexed amplifiers or shared amplifiers. The switch 174 determines the "sensing polarity" of the cardiac signal by selectively closing the appropriate switches, as is also known in the art. In this way, the clinician may program the sensing polarity independent of the stimulation polarity. Each sensing circuit, 182 and 184, preferably employs one or more low power, precision amplifiers with programmable gain and/or automatic gain control, bandpass filtering, and a threshold detection circuit, as known in the art, to selectively sense the cardiac signal of interest. The automatic gain control enables the device 110 to deal effectively with the difficult problem of sensing the low amplitude signal characteristics of atrial or ventricular fibrillation The outputs of the atrial and ventricular sensing circuits, 182 and 184, are connected to the microcontroller 160 which, in turn, are able to trigger or inhibit the atrial and ventricular pulse generators, 170 and 172, respectively, in a demand fashion in response to the absence or presence of cardiac activity in the appropriate chambers of the heart.

For arrhythmia detection, the device 110 utilizes the atrial and ventricular sensing circuits, 182 and 184, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 160 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, defibrillation shocks, collectively referred to as "tiered therapy").

Cardiac signals are also applied to the inputs of an analog-to-digital (A/D) data acquisition system 190. The data acquisition system 190 is configured to acquire intracardiac electrogram signals, convert the raw analog data into a digital signal, and store the digital signals for later processing and/or telemetric transmission to an external device 202. The data acquisition system 190 is coupled to the right atrial lead 120, the coronary sinus lead 124, and the right ventricular lead 130 through the switch 174 to sample cardiac signals across any pair of desired electrodes.

The microcontroller 160 is further coupled to a memory 194 by a suitable data/address bus 196, wherein the programmable operating parameters used by the microcontroller 160 are stored and modified, as required, in order to customize the operation of the stimulation device 110 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the heart within each respective tier of therapy.

Advantageously, the operating parameters of the prophylactic pacer/defibrillator may be non-invasively programmed into the memory 194 through a telemetry circuit 200 in telemetric communication with the external device 202, such as a programmer, transtelephonic transceiver, or a diagnostic system analyzer. The telemetry circuit 200 is activated by the microcontroller by a control signal 206. The telemetry circuit 200 advantageously allows intracardiac electrograms and status information relating to the operation of the device (as contained in the microcontroller 160 or memory 194) to be sent to the external device 202 through an established communication link 204.

In a preferred embodiment, stimulation device 110 further includes a physiologic sensor 208, commonly referred to as a "rate-responsive" sensor because it is typically used to adjust pacing stimulation rate according to the exercise state of the patient. However, the physiological sensor 208 may further be used to detect changes in cardiac output, changes in the physiological condition of the heart, or diurnal changes in activity (e.g., detecting sleep and wake states). Accordingly, the microcontroller 160 responds by adjusting the various pacing parameters (such as rate, AV Delay, V-V Delay, etc.) at which the atrial and ventricular pulse generators, 170 and 172, generate stimulation pulses. The type of sensor used is not critical and is shown only for completeness. As further shown in FIG. 6, the device 110 is shown as having an impedance measuring circuit 212 which is enabled by the microcontroller 160 via a control signal 214.

The stimulation device additionally includes a pair of batteries 210 and 211. Battery 210, which is a carbon monofluoride ($CF_x$) battery or other high capacity/low rate power source, provides power for all devices functions except defibrillation shocks. Battery 211, which is a lithium magnesium oxide ($LiMnO_2$) battery or other low capacity/high rate power source, provides power for ventricular defibrillation only. FIG. 6, which is discussed below, provides a schematic illustration of the general electrical circuits of stimulation device 110, particularly illustrating the separate pacing/control and defibrillation circuits powered by the separate batteries. It will be apparent to those skilled in the art that a prophylactic ICD may be formed having only defibrillation capabilities (e.g., for patients that do not require pacing assistance), in which case only battery 211 would be needed.

Since the stimulation device 110 is intended to operate as a "one shot" defibrillator, it must detect an occurrence of ventricular fibrillation and automatically apply appropriate electrical shock therapy to the heart so as to terminate the detected ventricular fibrillation. To this end, the microcontroller 160 further controls a ventricular shocking circuit 216 by way of a control signal 218. The shocking circuit 216 generates shocking pulses of high energy (11 to 40 joules), as controlled by the microcontroller 160. Such shocking pulses are preferably applied to the heart between the RV coil electrode 36 and device case (electrode 40). In other implementations wherein additional coil electrodes are implanted within the heart, the defibrillation pulse may be delivered between the RV coil and one of the other coils. In that alternative implementation, the housing 140 may act as an active electrode in combination with the RV electrode 36 or as part of a split electrical vector using the other coil electrodes. The defibrillation shocks are delivered asynchronously (in case of false detection of fibrillation) and pertain exclusively to the treatment of ventricular fibrillation.

Selected Circuit Features of the Prophylactic Pacer/Defibrillator

Figure 7:
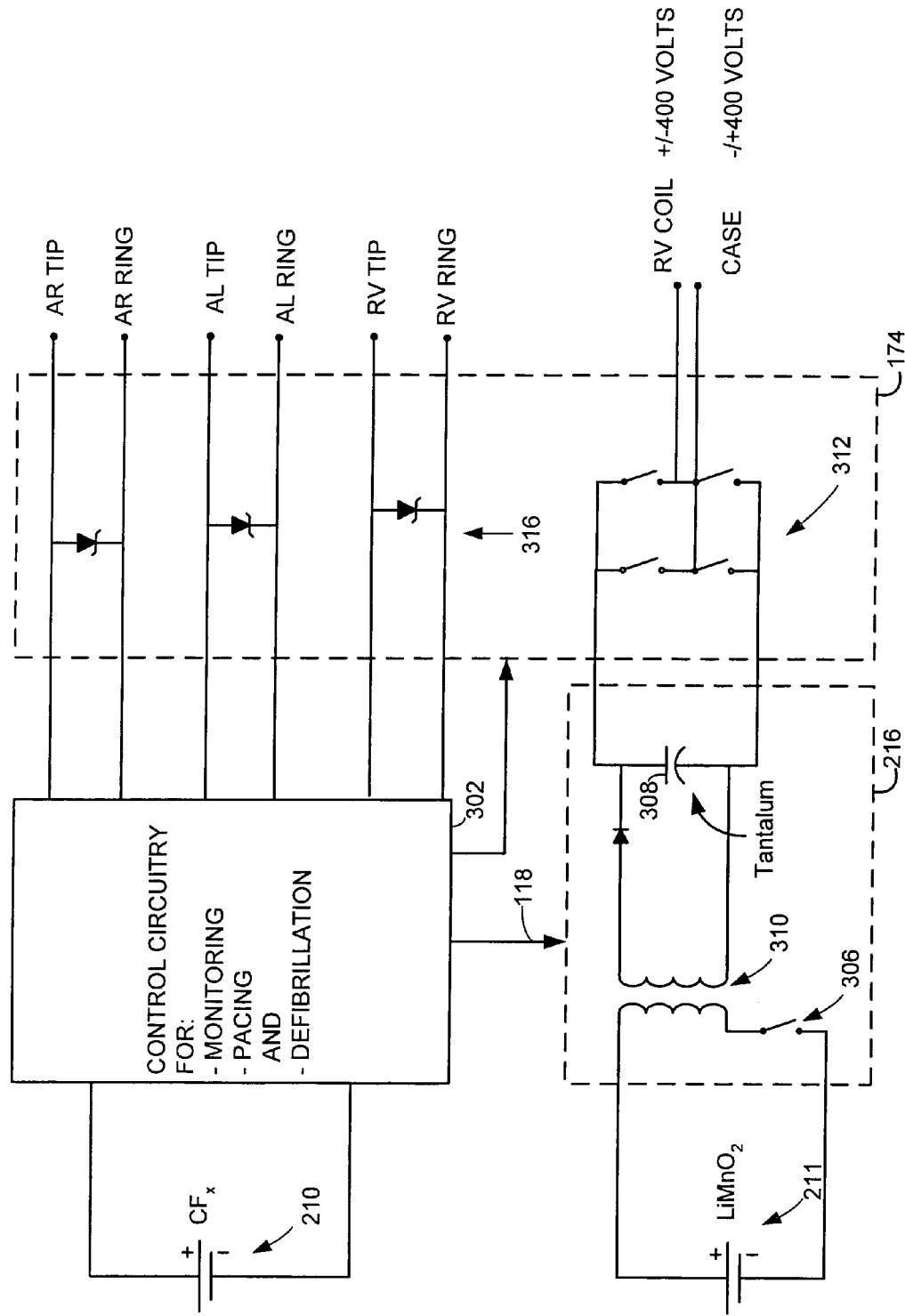
FIG. 7 is block diagram (partially in schematic form) of selected components of the prophylactic pacer/defibrillator device of FIG. 5.

Selected features of the prophylactic pacer/defibrillator of FIG. 6 are illustrated in the diagram of FIG. 7. As shown, separate power sources are provided for powering all control, monitoring and pacing functions and for separately powering delivery of defibrillation shocks. Carbon monofluoride battery 210 provides power for all pacing, monitoring and control functions, including the detection of ventricular fibrillation. In FIG. 7, a block 302 represents all corresponding pacing, monitoring and control circuit components (which includes all components shown in FIG. 6, with the exception of switch 174 and ventricular shocking circuit 216.) A separate lithium manganese dioxide battery 302 provides power exclusively for the delivery of defibrillation shocks. By providing a separate power source for delivering defibrillation shocks, the separate power source need to be capable of delivering shocks and also providing power for long-term pacing and monitoring. Rather, the separate power source can be optimized for delivering power for defibrillation shocks and can be completely depleted during use, with the carbon monofluoride battery still providing power for monitoring pacing. This allows much smaller, lighter, and less-expensive power sources to be used than the conventional SVO power source used in full-service ICDs of the type illustrated in FIGS. 1–2, which must be capable of delivering a potentially large number of defibrillation shocks as well as providing sustained power for all pacing, monitoring and capacitor reformation functions.

Thus, although two batteries are required in the configuration of FIG. 7, collectively the two batteries are substantially smaller, lighter and less expensive than a single SVO large battery, thus reducing the size, weight and cost of the prophylactic pacer/defibrillator as compared to full-service ICDs. In particular, the secondary power source, i.e. battery 211, is configured to deliver six to ten defibrillation shocks. Typically, the prophylactic pacer/defibrillator is programmed to allow only six consecutive defibrillation shocks to be delivered in response to a single episode of the trigger fibrillation. The battery 211, however, is preferably designed to have the capacity to provide a few additional defibrillation pulses, primarily as a safety margin. Although FIG. 7 is described with reference to a specific example employing one carbon monofluoride battery and one lithium magnesium oxide battery, other appropriate power sources may instead be employed. Preferably, battery 211 is configured to be able to initially store an amount of energy in the range of 200 to 800 joules and to be able to initially provide an output current in the range of 0.5 to 1.0 amperes. In general, battery 210 can comprise any low rate/high-capacity power cells or combination of power cells such as lithium iodide power cells; whereas battery 211 can comprise any relatively high rate/low capacity power cells or combination of power cells such as SVO cells and CFx/SVO hybrids power cells.

Upon detection of ventricular fibrillation by control circuit 302, a control signal is sent a long line 218 to ventricular shocking circuit 216, which causes switch 306 to close to allow current from battery 211 to begin charging tantalum capacitor 308 via voltage transformer 310. Once the capacitor has reached its maximum voltage, a full bridge switch 312 (which is a component of overall configuration switch 174 of FIG. 6) is selectively closed to deliver the energy stored within the capacitor to the heart of the patient as a biphasic shock via the right ventricular coil and the case. Unlike the conventional ICD configuration illustrated in FIGS. 1–2, cut-off switches are not provided along the right atrial, left atrial and right ventricular tip and ring leads, at least for the purposes of preventing currents generated by the shocking pulse from propagating back into the device via those leads. Rather, much smaller, lighter and less-expensive zener diodes 316 are positioned along the leads, as shown, for shunting inbound current along one lead outbound on another lead. The use of a zener diode allows for pacing in the negative polarity and shunting of defibrillation currents in the positive polarity. The choice of particular zener diode is a function of the maximum pacing voltage allowed, e.g. if the maximum pacing voltage 7.5V, a 10V zener is preferred. In the specific example of FIG. 7, a single zener diode interconnects each corresponding tip and ring electrode. In other implementations, zener diodes could instead interconnect other combinations of leads. A variety of specific configurations may be provided, so long as the zener diodes are position to route any inbound currents back outbound. In any case, by employing the smaller, lighter and less-expensive zener diodes rather than the cut-off switches, the overall cost, size, and weight of the prophylactic pacer/defibrillator is reduced over full-service ICDs. Moreover, logic required to coordinate opening of the switches can be eliminated.

Figure 1:
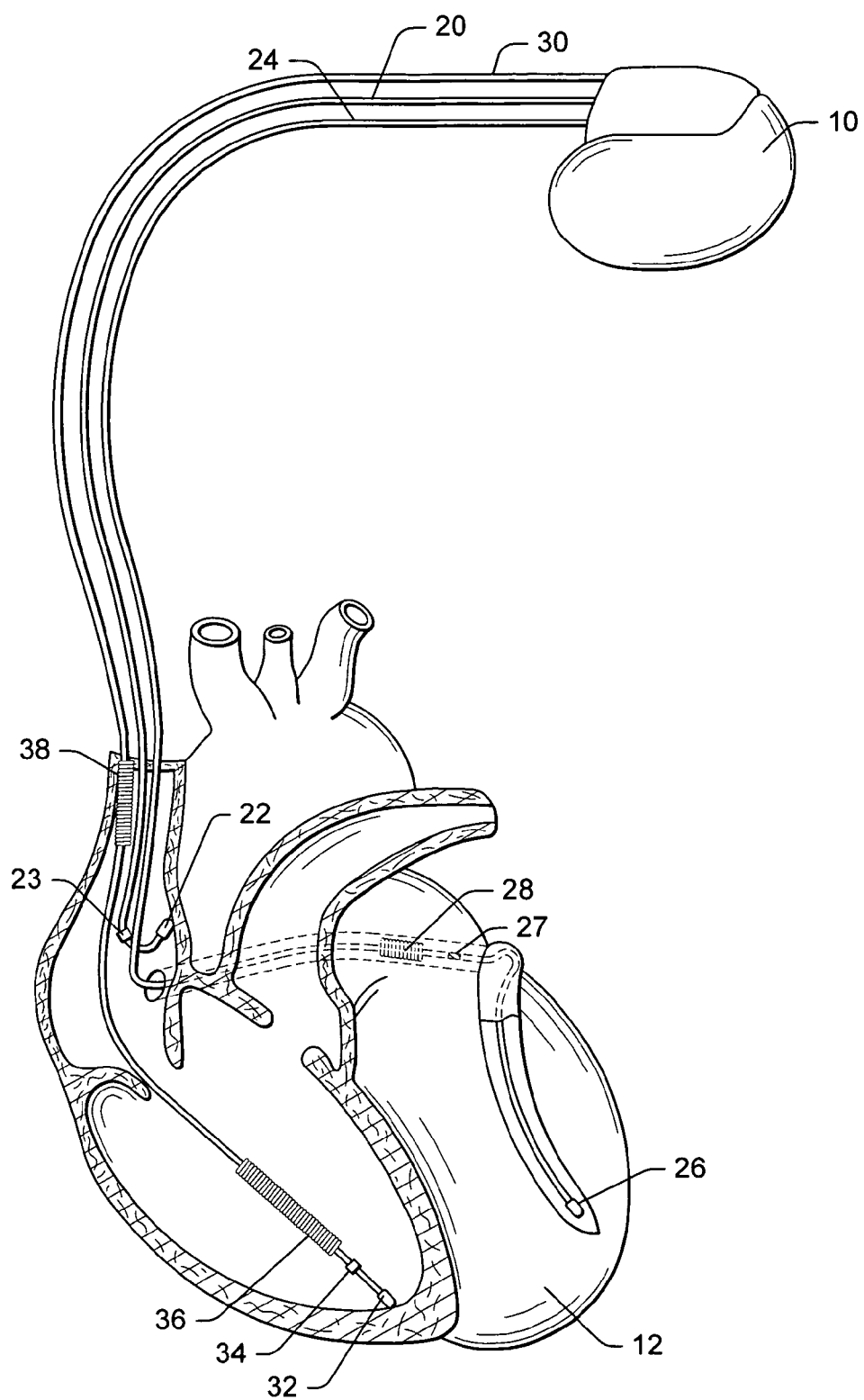
FIG. 1 illustrates a conventional ICD and associated leads.
Figure 2:
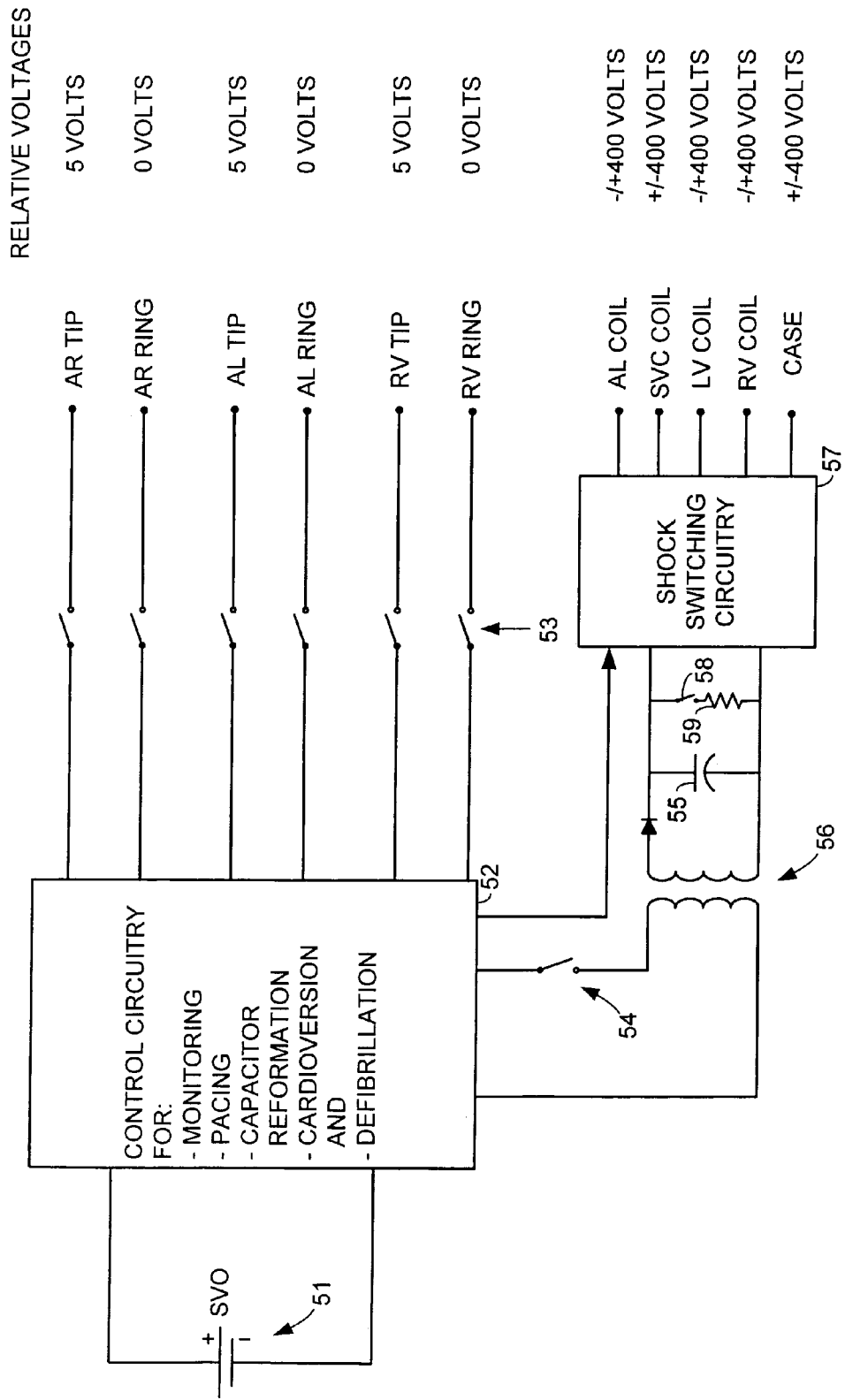
FIG. 2 is block diagram (partially in schematic form) of selected components of the conventional ICD of FIG. 1.
Figure 3:
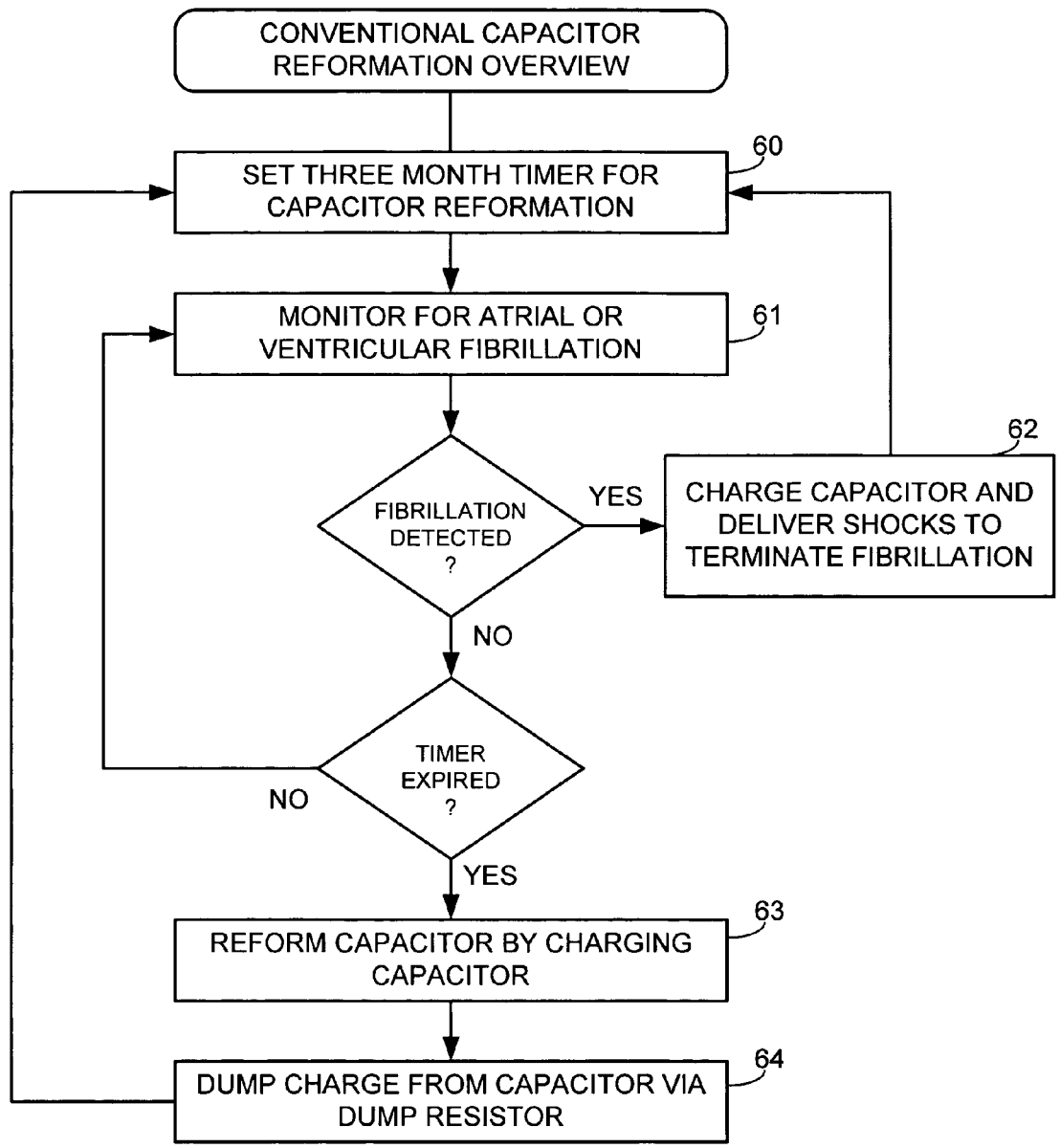
FIG. 3 is a flow chart providing an overview of capacitor reformation as performed by the conventional ICD of FIG. 1.

Note also that, in contrast with the conventional full-service ICD of FIGS. 1–2, prophylactic pacer/defibrillator of FIG. 7 does not include a dump resistor for dumping charge from a capacitor 308. As already explained, such dump resistors are employed in connection with capacitor reformation to dump charge stored with a capacitor. The prophylactic pacer/defibrillator of FIG. 7 does not perform capacitor reformation and hence no dump resistor is required. It is possible, however, for the capacitor to be charged in expectation of delivering a defibrillation shock due to the detection of ventricular fibrillation, but then the fibrillation spontaneously reverts to a normal sinus rhythm, thus leaving some charge contained within the capacitor. In this case, the system simply lets the charge slowing bleed off. By eliminating the dump resistor and the dump resistor switch, the prophylactic pacer/defibrillator is therefore smaller, lighter and less complex than a full-service ICD that requires a dump resistor. Moreover, logic required to coordinate the operation of the dump resistor is not needed. Additionally, of course, logic required to coordinate reformation of the capacitor need not be provided either.

Although FIG. 7 illustrates a tantalum capacitor, other capacitors may be used as well. In particular, as described below in connection with FIG. 11, an otherwise conventional aluminum oxide capacitor can instead be used, but simply not reformed. By employing a tantalum capacitor or by employing an aluminum oxide capacitor but not reforming the aluminum oxide capacitor, it will typically require about 10 seconds longer to charge capacitor to deliver a first defibrillation shock. Hence, a first defibrillation pulse typically cannot be delivered as promptly as in a full-service ICD. However, in comparison with the time delay that would otherwise occur between the onset of the ventricular fibrillation and the arrival of paramedics with an external defibrillator, the prophylactic pacer/defibrillator can still deliver defibrillation shocks quite promptly. Also, note that, rather than providing a single physical capacitor, two or more smaller capacitors can instead be employed for storing the charge associated with a single defibrillation pulse.

Also with respect to FIG. 7, note that no left ventricular coil, SVC coil or left atrial coil is provided. No left atrial coil is provided because cardioversion therapy is not delivered. No SVC coil is provided since defibrillation shocks use the case as a return electrode. No left ventricular coil is provided since defibrillation therapy is delivered exclusively via the right ventricular coil and device case. This reduces the cost and complexity of the leads, as well as reducing the size, cost and complexity of any switching circuitry required to coordinate the use of the additional electrodes. In addition, by not providing for cardioversion therapy, a reduction in the complexity of the software to be employed within microcontroller 160 can be achieved. Moreover, switches that would otherwise be required to select between the various coil electrodes are not required, thus reducing size weight and complexity of the device as compared to full-service ICDs. In other implementations, however, a left atrial coil can be provided with the device designed to additionally perform atrial cardioversion therapy. Care should be taken to ensure that cardioversion shocks do not completely deplete the power source, thus preventing delivery of a ventricular defibrillation shock when needed. In one example, the device suspends cardioversion therapy once the power source has been depleted to the point where is can delivery only about six defibrillation shocks. An SVC coil can optionally be provided for use in combination with the RV coil for delivering defibrillation shocks, which is described below in connection with FIGS. 10–11. Likewise, a left ventricular coil electrode can also to be provided, thus allowing defibrillation shocks to be delivered between the left and right ventricular coils. As can be appreciated, a wide range of specific embodiments may be provided, which are less complex and expensive than a full-service ICD and yet which provided some degree of cardioversion or defibrillation therapy not provided by a conventional pacemaker.

Insofar as the amount of charge to be delivered within each individual defibrillation pulse, circuitry 302 controls shocking circuit 216 to deliver a fixed amount of charge or an amount programmed by a physician using an external programming device. In any case, no induction testing is performed—either for the purposes of setting the pulse magnitude or for verifying that the prophylactic pacer/defibrillator properly detects episodes of ventricular fibrillation. Since no induction testing is performed by the device itself, battery 211 need not contain sufficient capacity to provide energy both for the shocks used during induction testing and for any defibrillation shocks delivered subsequently. Note, that induction testing can be performed using external equipment, i.e. fibrillation can be induced to verify that the implanted device properly detects the fibrillation, but with an external defibrillator used to actually defibrillate the heart.

Exemplary voltage levels for the right ventricular coil and case electrodes are also shown in FIG. 7. As with conventional full-service ICDs, there is an 800 volt difference between the right ventricular coil and the case for delivering a high-voltage defibrillation shock. However, rather than holding the tip and ring electrode voltages to intermediate voltages, the ring voltages are held at the same voltage as the coil, e.g. +/−400 volts in this example. Thus, there is no voltage difference between the various ring electrodes and the case during delivery of a defibrillation shock and so zener diodes need not be provided between the ring electrodes and the case. Hence, a reduction of the total number of shunting diodes is achieved as compared to a configuration wherein the tip and ring electrodes are at voltages midway between the voltages of the case and the right ventricular coil. For pacing, the various tip electrodes are held to voltages that typically differ by +/−5 volts from that of the ring electrodes to allow for 5 volt pacing pulses. The voltages of the tip and ring electrodes are not listed in FIG. 7 since the voltages depend upon whether pacing is being delivered or whether a shock is being delivered and further depend on the phase of the shock. Circuitry for holding the ring electrodes to the same voltage as the RV coil is not explicitly shown in FIG. 7, but forms a part of configuration switch 174.

Figure 4:
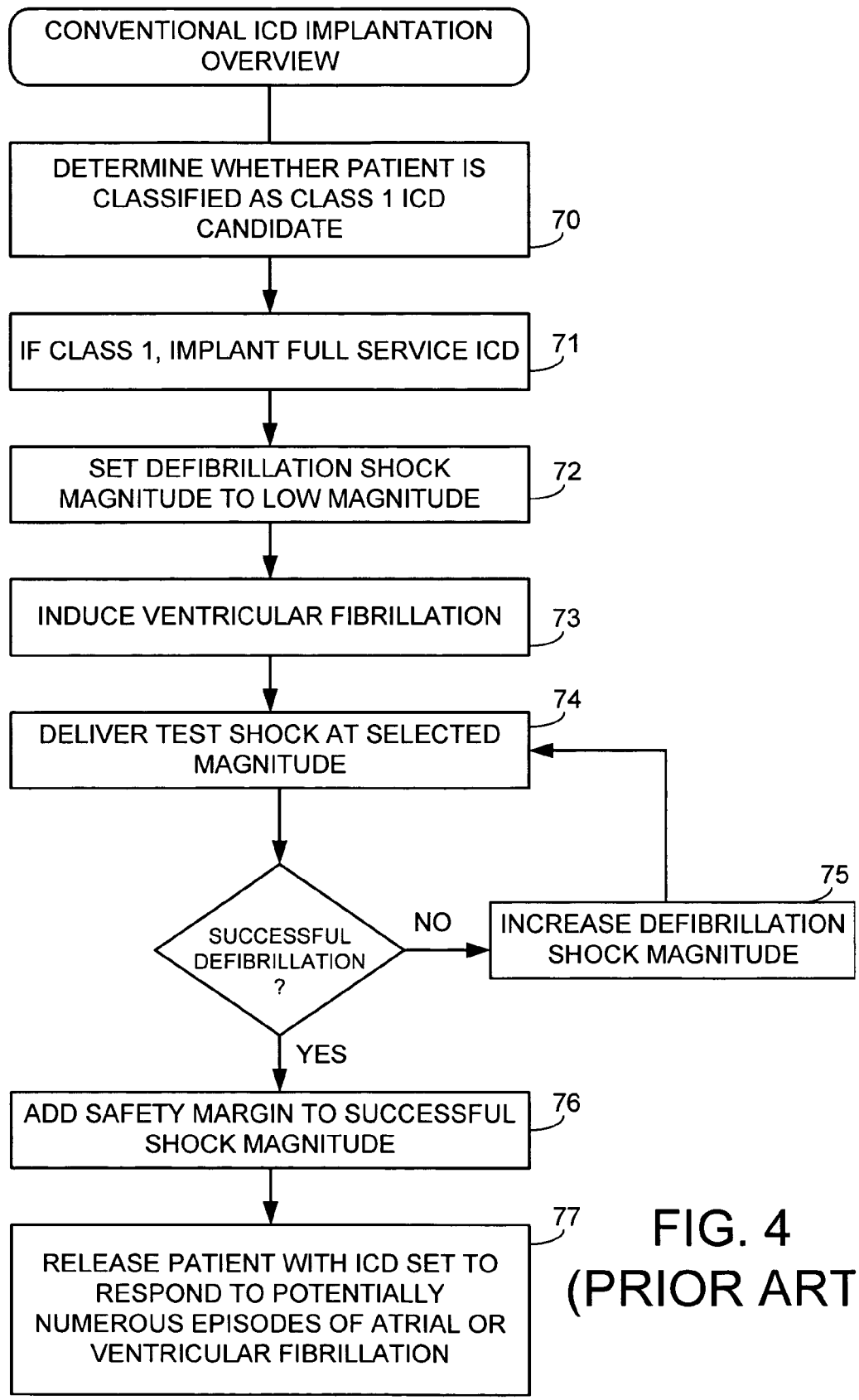
FIG. 4 is a flow chart providing an overview of an implantation procedure for the conventional ICD of FIG. 1, in which fibrillation induction is performed to set shock magnitudes.
Figure 8:
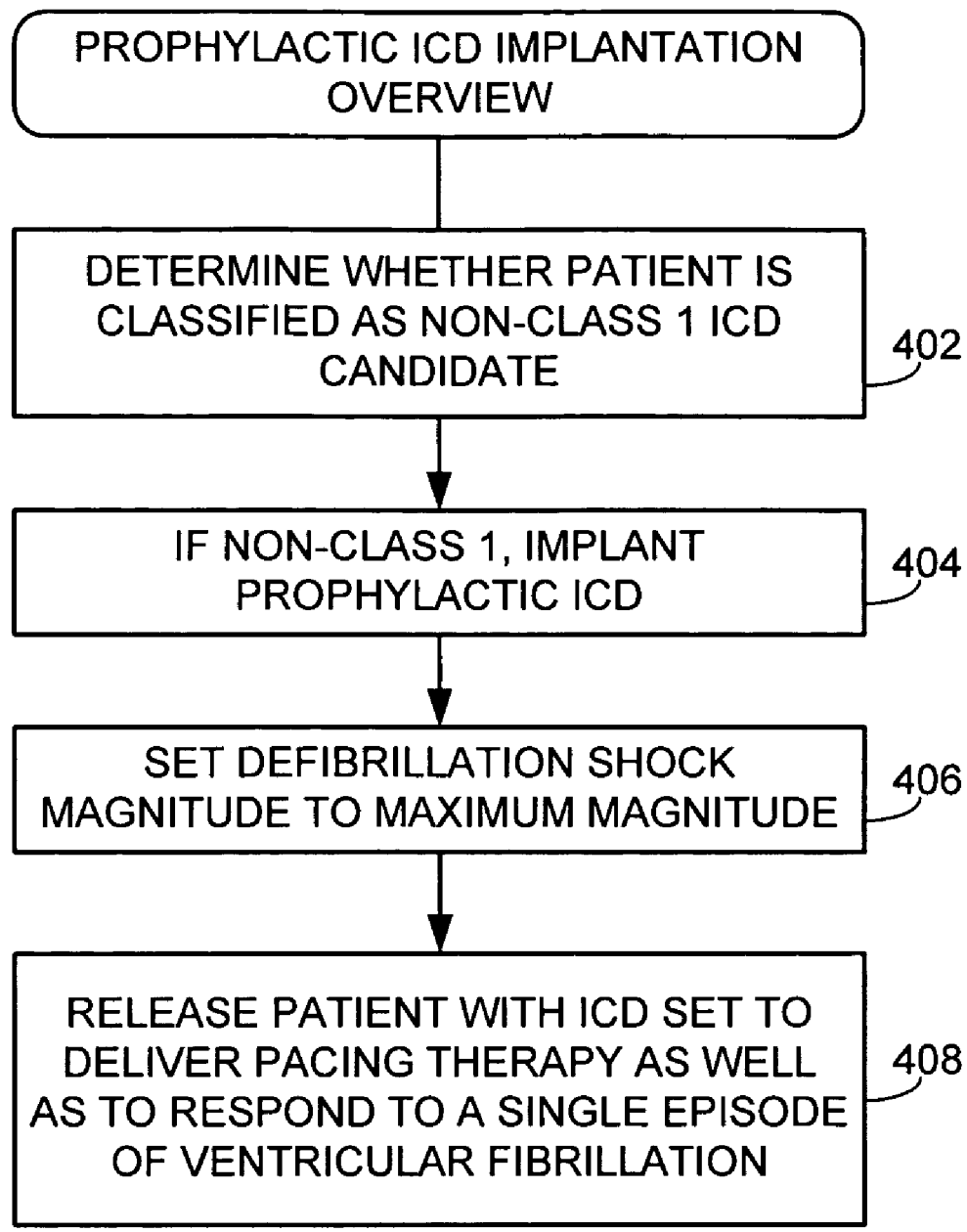
FIG. 8 is a flow chart providing an overview of an implantation procedure for the prophylactic pacer/defibrillator device of FIG. 5, in which no fibrillation induction is performed.
Figure 9:
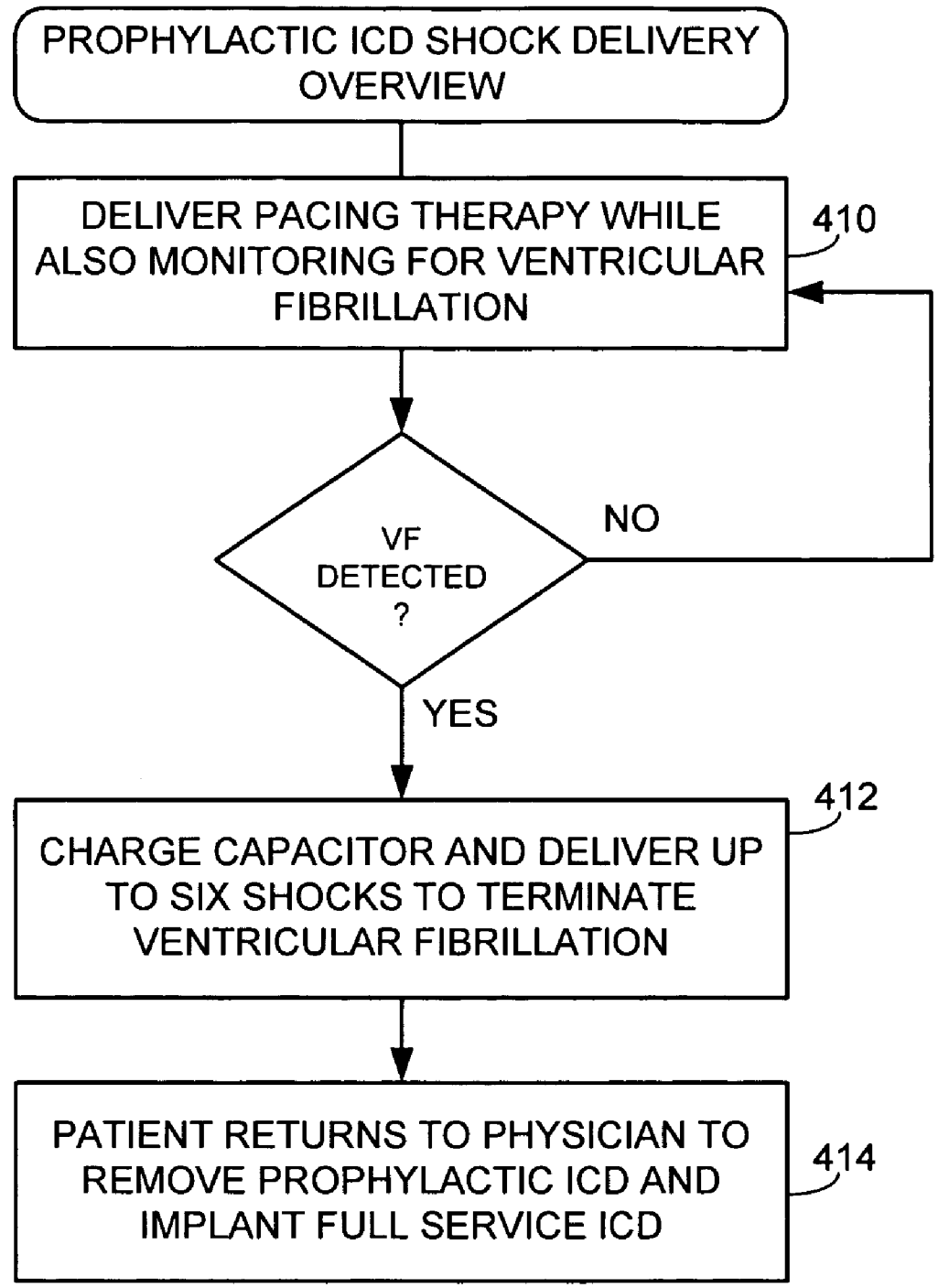
FIG. 9 is a flow chart providing an overview of the delivery of shocks by the prophylactic pacer/defibrillator device of FIG. 5, in which capacitor reformation is not periodically performed.

FIGS. 8 and 9 summarize the implantation and shocking procedures for the prophylactic pacer/defibrillator. Referring first to FIG. 8, at step 402, a determination is made as to whether the patient is classified as a non-class 1 ICD candidate. If non-class 1, the prophylactic pacer/defibrillator is implanted within the patient, at step 404. (If the patient is instead a class 1 candidate, a full-service ICD is implanted.) After implantation of the prophylactic pacer/defibrillator, the fibrillation shock magnitude is set to a maximum shock magnitude, at step 406. Thus, in contrast with the implantation procedure of the full-service ICD of FIG. 4 wherein a fibrillation induction procedure is performed, with the prophylactic pacer/defibrillator, no such procedure is required. Rather, after the shock magnitude has been set, the patient is sent home, at step 408, with the pacer/defibrillator set to provide pacing therapy and to additionally respond to a single episode of ventricular fibrillation. One or more follow-up sessions may be scheduled to allow the position to verify that the prophylactic pacer/defibrillator is functioning properly.

In use, as shown in FIG. 9, the prophylactic pacer/defibrillator delivers any necessary pacing therapy, at step 410, while also monitoring for the onset of ventricular fibrillation. If ventricular fibrillation is detected, the prophylactic pacer/defibrillator charges its internal capacitor, at step 412, and delivers up to six shocks in the succession to terminate the episode of ventricular fibrillation. After the single episode has been terminated, the patient returns to his or her physician, step 414, to have the prophylactic pacer/defibrillator replaced with a full-service ICD. In this manner, a patient who would otherwise only receive a pacemaker, instead receives a device capable of delivering pacing therapy and also responding to a single episode of ventricular fibrillation, thus likely saving the patient's life in the event VF occurs.

Alternative Prophylactic Pacer/Defibrillator System

Figure 10:
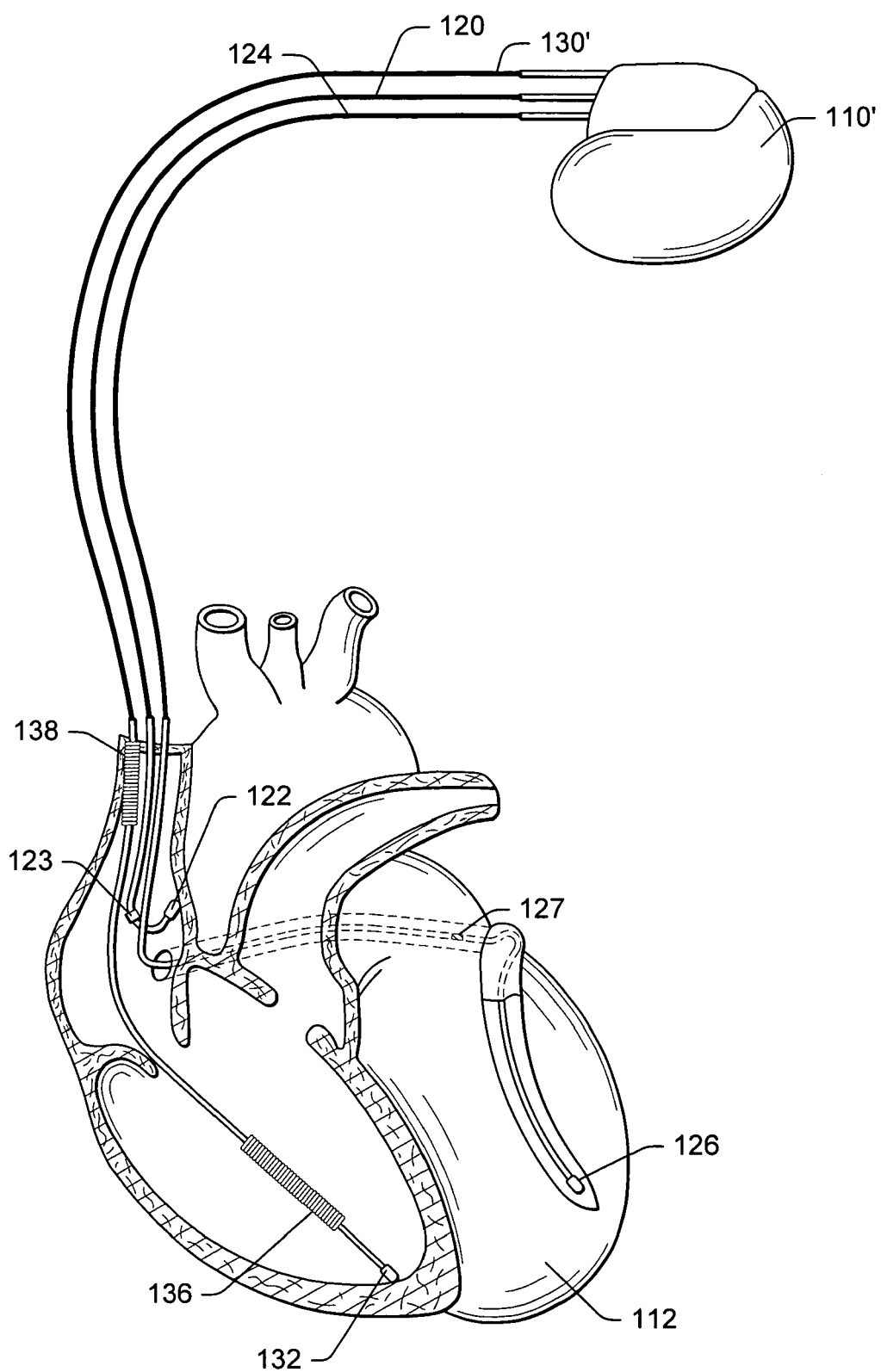
FIG. 10 illustrates a prophylactic pacer/defibrillator device and three leads, collectively configured in accordance with an alternative embodiment that includes an SVC coil.
Figure 11:
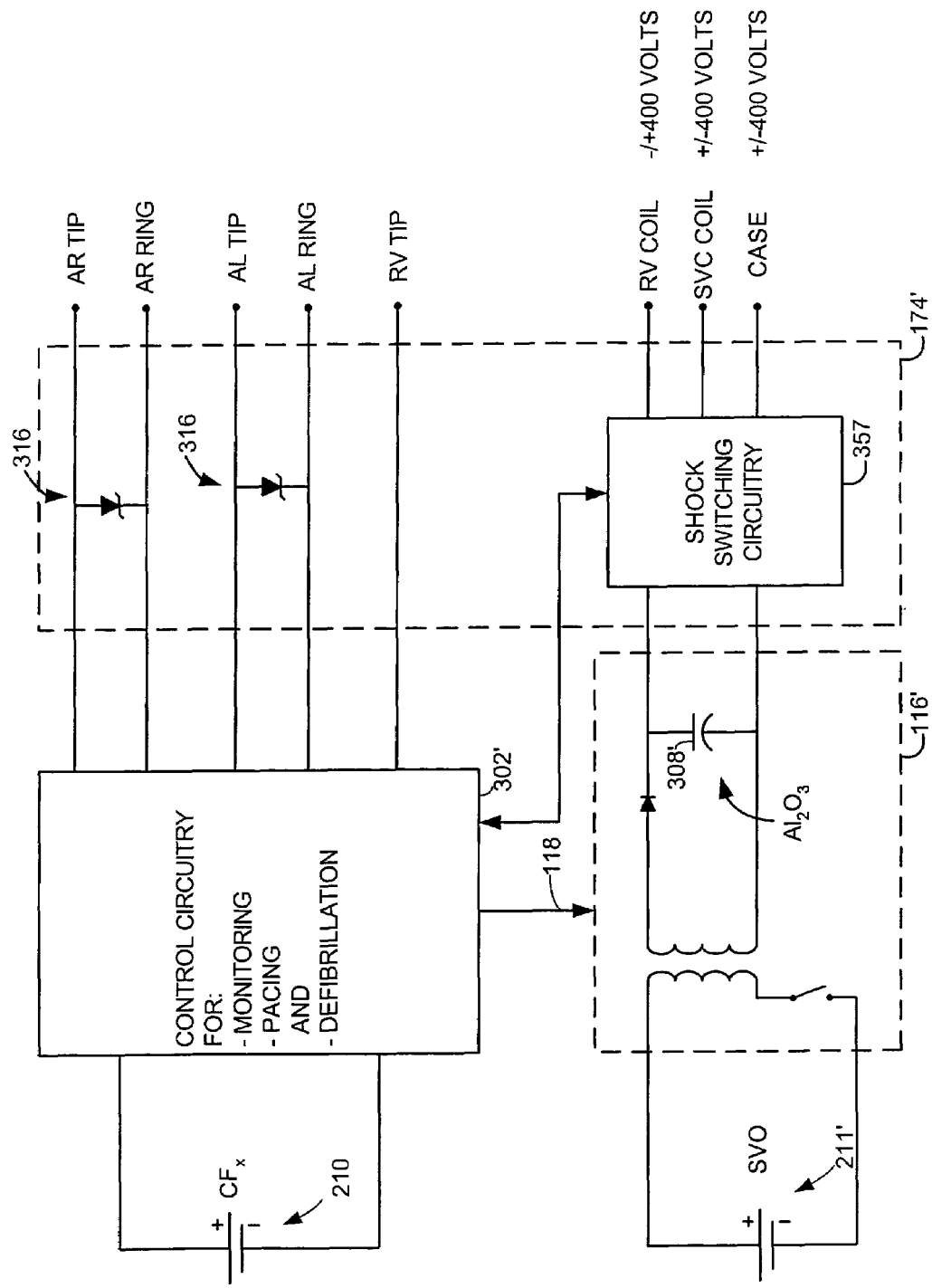
FIG. 11 is block diagram (partially in schematic form) of selected components of the alternative prophylactic pacer/defibrillator device of FIG. 10.

With reference to FIGS. 10 and 11, additional features of the prophylactic ICD will be described, which may be used in addition to, or alternatively to, features already set forth.

An alternative prophylactic pacer/defibrillator 110' is illustrated in FIG. 10 along with various sensing/pacing/shocking leads. The alternative device and its leads are similar to the system of FIGS. 5–9 and only pertinent differences will be described in detail. As before, a right atrial lead 120 having an atrial tip electrode 122 and an atrial ring electrode 123 is provided. In addition, a coronary sinus lead 124 having a left ventricular tip electrode 126 and a left atrial ring electrode 127 is provided. However, right ventricular lead 130' differs from lead 130 of FIG. 5. Both include a right ventricular tip electrode 132 and a right ventricular coil electrode 136, but lead 136' also includes an SVC coil electrode 138. Moreover, right ventricular lead 130' does not include a ring electrode. Rather right ventricular pacing is performed by applying voltages between the RV tip 132 and the RV coil, which (as in the preceding embodiment) are held at voltages relatively close to one another. Given the added SVC coil, additional insulation may be required along lead 130'.

Selected internal features of the prophylactic device of FIG. 10 are illustrated in FIG. 11. As before shown, separate power sources are provided. However, in this embodiment, an SVO battery 211' is used for providing power for defibrillation shocks, along with a carbon monofluoride battery 210 used for providing power for all other sources. The SVO battery, however, need not be capable of delivering potentially hundreds of defibrillation shocks as with conventional full-services ICDs. Rather, it need only be sufficient to provide power for a relatively small number (e.g., six) defibrillation shocks to be delivered in response to a single episode of ventricular fibrillation. Also, whereas a tantalum capacitor 308 was employed in the preceding embodiments, in the embodiment of FIG. 11, an aluminum oxide capacitor 308' is instead employed. As before, however, the capacitor is not reformed and no dump resistor is provided. Since the aluminum oxide capacitor is not reformed, it will take longer to charge the capacitor for delivery of a first shock. Nevertheless, as already noted, the elimination of reformation permits use of a much smaller power supply than would otherwise be required.

With the elimination of the RV ring electrode, pacing is performed between the RV coil and the RV tip electrodes. More specifically, for RV pacing, appropriate signals are sent from control circuitry 302' to shock switching circuitry 357 (which is a component of overall electrical configuration switch 174') to connect the RV coil electrode. Pacing pulses are delivered to the RV tip electrode (powered by the carbon monofluoride power cell). The RV coil is used as the return electrode. By eliminating the RV ring electrode, overall cost is reduced as compared to systems employing an RV ring. Moreover, fewer zener shunt diodes (316) are thereby required. The ability to pace via the RV tip and RV coil electrodes is achieved, in part, by holding the RV tip voltage relatively close to the voltage of the RV coil during pacing—typically with a 5 volt difference. As before, the voltages of the other ring electrodes are held at the same voltage as the RV coil at least during delivery of a defibrillation shock. The voltages of the various tip and ring electrodes are not listed in FIG. 11 since the voltages depend upon whether pacing is being delivered or whether a shock is being delivered and further depend on the phase of the shock. Circuitry for holding the atrial ring electrodes to the same voltage as the RV coil is not explicitly shown in FIG. 11, but forms a part of configuration switch 174.

With the addition of the SVC coil, defibrillation shocks may be delivered between the RV coil and SVC coil or between the RV coil and the device case (as before) or using all three electrodes. A full bridge switch may be incorporated within switch 357 for providing biphasic shocking pulses. In the preferred implementation of FIG. 11, the shock is delivered between the RV coil and the SVC coil to reduce a defibrillation threshold.

While the invention herein disclosed has been described by means of specific embodiments and applications thereof, numerous modifications and variations could be made thereto by those skilled in the art without departing from the scope of the invention set forth in the claims.

What is claimed is:

1. An implantable pacemaker/defibrillation device comprising:
    pacing pulse generation circuitry;
    defibrillation shock generation circuitry;
    ventricular tip and ring electrodes and atrial tip and ring electrodes for delivering pacing pulses;
    a ventricular coil electrode for delivering shocking pulses;
    a switch operative to hold the atrial and ventricular ring electrodes at a voltage equal to that of the ventricular coil electrode during shocking pulse delivery and to hold a ring electrode at a voltage relative to a tip electrode to deliver a pacing pulse;
    a first power source operative to provide power for the pacing pulse generation circuitry; and
    a second power source operative to provide power for the defibrillation shock generation circuitry.

2. An implantable prophylactic pacemaker/defibrillation device for delivering defibrillation shocks in response to only a single episode of ventricular fibrillation, the device comprising:
    pacing pulse generation circuitry selectively coupled to ventricular tip and ring electrodes and right atrial tip and ring electrodes for delivering pacing pulses to the heart of the patient;
    defibrillation shock generation circuitry including a shock capacitor, the defibrillation shock generation circuitry selectively coupled to a right ventricular coil electrode and a device housing electrode for delivering a ventricular defibrillation shock to the heart of a patient;
    a first power source operative to provide power for the pacing pulse generation circuitry; and
    a second power source permanently electrically decoupled from the pacing pulse generator and operative to provide power only for the defibrillation shock generation circuitry, the second power source configured to provide sufficient power for delivering defibrillation shocks only in response to the single episode of ventricular fibrillation; with
    the defibrillation shock generation circuitry including non-reformation-based charging circuitry operative to charge the shock capacitor using the second power source for delivering the defibrillation shocks without prior capacitor reformation;
    wherein the defibrillation shock generation circuitry and the pacing pulse generation circuitry are operative to hold the ventricular and atrial ring electrodes at a voltage equal to that of the right ventricular coil.

3. The implantable device of claim 2 wherein the shock capacitor is a tantalum capacitor.

4. The implantable device of claim 2 wherein the shock capacitor is an aluminum oxide capacitor.

5. The implantable device of claim 2 wherein the defibrillation shock generation circuitry and the second power source are configured to slowly charge the shock capacitor over a period of time not less than 11 seconds prior to delivery of a first defibrillation shock.

6. The implantable device of claim 2 configured to be capable of delivering up to six defibrillation shocks in response to the single episode of ventricular fibrillation.

7. The implantable device of claim 2 wherein the individual defibrillation shocks have energies in the range of 10–40 joules.

8. The implantable device of claim 1 wherein:
    the first power source is a low rate, long life power source; and
    the second power source is a high rate, short life power source.

9. The implantable device of claim 8 wherein:
    the first power source is a polycarbon monofluoride (CFx) power source; and the second power source is a lithium manganese dioxide (LiMnO2) power source.

10. The implantable device of claim 2 further comprising control circuitry operative to control the pacing pulse generation circuitry and the defibrillation shock generation circuitry and wherein the first power source additionally provides power for the control circuitry.

11. The implantable device of claim 2 wherein shunt diodes interconnect the right ventricular tip and ring electrodes and right atrial tip and ring electrodes, respectively.

12. The implantable device of claim 2 wherein the pacing pulse generation circuitry is selectively coupled to the right ventricular coil electrode and a ventricular tip electrode and the pacing pulse generation circuitry is operative to deliver pacing pulses to the right ventricle between the right ventricular tip electrode and the right ventricular coil.

13. The implantable device of claim 2 wherein the defibrillation shock generation circuitry is also selectively coupled to a superior vena cava (SVC) electrode for use in delivering defibrillation shocks in combination with the right ventricular coil.

14. The implantable device of claim 13 wherein the SVC electrode is hard-connected to the device.

* * * * *